United States Patent [19]

VandenBerg

[11] Patent Number: Plant 6,949

[45] Date of Patent: Jul. 25, 1989

[54] CHRYSANTHEMUM PLANT NAMED KORY

[75] Inventor: Cornelis P. VandenBerg, Salinas, Calif.

[73] Assignee: Yoder Brothers, Inc., Barberton, Ohio

[21] Appl. No.: 219,010

[22] Filed: Jul. 14, 1988

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Kory particularly characterized as to uniqueness by the combined characteristics of flat capitulum form; decorative capitulum type; yellow ray floret color; diameter across face of capitulum of up to 10 cm at maturity; uniform eight week photoperiodic flowering response to short days; medium plant height when grown as a pinched pot mum; semi-spreading and prolific branching pattern; and recommended for both disbudded and spray pots.

3 Drawing Sheets

The present invention comprises a new and distinct cultivar of Chrysanthemum, botanically known as *Dendranthema grandiflora,* and referred to by the cultivar name Kory.

Kory, identified as 83748001, was originated from a cross made in a controlled breeding program in Salinas, Calif. in 1983.

The female parent and the male parent of Kory were both unnamed seedlings, identified respectively as 77280F01 and 78702005.

Kory was discovered and selected as one flowering plant within the progeny of the stated cross by Cornelis P. VandenBerg in December 1983 in a controlled environment in Salinas, Calif.

The first act of asexual reproduction of Kory was accomplished when vegetative cuttings were taken from the initial selection in February 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Kory are firmly fixed and are retained through successive generations of asexual reproduction.

Kory has not been observed under all possible environmental conditions. The phenotype may vary significantly with variations in environment such as temperature, light intensity, and daylength.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Kory, which, in combination, distinguish this Chrysanthemum as a new and distinct cultivar:

1. Flat capitulum form.
2. Decorative capitulum type.
3. Yellow ray floret color.
4. Diameter across face of capitulum up to 10 cm at maturity when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Semi-spreading and prolific branching pattern.
8. Recommended for both disbudded and spray pots.

The accompanying photographic drawings show typical inflorescence and leaf characteristics of Kory, with the colors being as nearly true as possible with illustrations of this type.

Sheet 1 is a color photograph of Kory grown as a pinched disbudded pot mum.

Sheet 2 is a black and white photograph of three views of the inflorescence of Kory.

Sheet 3 is a black and white photograph showing the upper and under sides of the leaves of Kory at three stages of development (mature, intermediate and immature).

Of the commercial cultivars known to the inventor, the most similar in comparison to Kory is Yellow Favor, disclosed in U.S. Plant Pat. No. 5,819. Reference is made to Chart A, which compares certain characteristics of Kory to the same characteristics of Yellow Favor.

Similar traits are color, capitulum form and type, and plant height. Kory is less spreading, has a smaller capitulum diameter, and has a shorter flowering response period than Yellow Favor. In addition, tests have shown that under low light conditions Yellow Favor develops browning and rotting of the inner ray florets. Kory has not exhibited this trait in similar tests.

In the following description, color references are made to The Royal Horticultural Society Colour Chart. The color values were determined on plant material grown in Salinas, Calif. on Jan. 5, 1988.

Classification:

*Botanical.*—*Dendranthema grandiflora,* cv Kory.

*Commercial.*—Decorative disbud and spray pot mum.

INFLORESCENCE

A. Capitulum:

*Form.*—Flat.

*Type.*—Decorative.

*Diameter across face.*—Up to 10 cm at maturity.

B. Corolla of ray florets;

*Color (general tonality from a distance of three meters).*—Yellow.

*Color (upper surface).*—6A to 6B.

*Color (under surface).*—7D.

*Shape.*—Other ray florets are spooned, with spoon length of 30% to 50% of the total length of the ray floret. Inner ray florets are first, straight, oblong.

C. Corolla of disc florets:

*Color (mature).*—2A.

*Color (immature).*—145B. Very few disc florets present, covered by the inner rows of ray florets.

D. Reproductive organs:

*Androecium.*—Present on disc florets only; very scant pollen.

*Gynoecium.*—Present on both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Semi-spreading and prolific.

B. Foliage:

*Color (upper surface).*—147A.

*Color (under surface).*—147B.

*Shape.*—Lobed, rounded and very slightly serrated.

CHART A

COMPARISON OF KORY AND YELLOW FAVOR

| | Kory | Yellow Favor |
|---|---|---|
| Ray floret color | Yellow | Yellow |
| Capitulum form and type | Flat Decorative | Flat Decorative |
| Branching pattern | Semi-spreading and prolific | Spreading |
| Diameter across face of capitulum | Up to 10 cm | Up to 12 cm |
| Plant height | Medium | Medium |
| Flowering response period | 8 weeks | 9 weeks |

COMPARISONS MADE OF PLANTS GROWN AS PINCHED DISBUDDED POT MUMS IN SALINAS, CALIFORNIA

I claim:

1. A new and distinct Chrysanthemum plant named Kory, as described and illustrated.

* * * * *

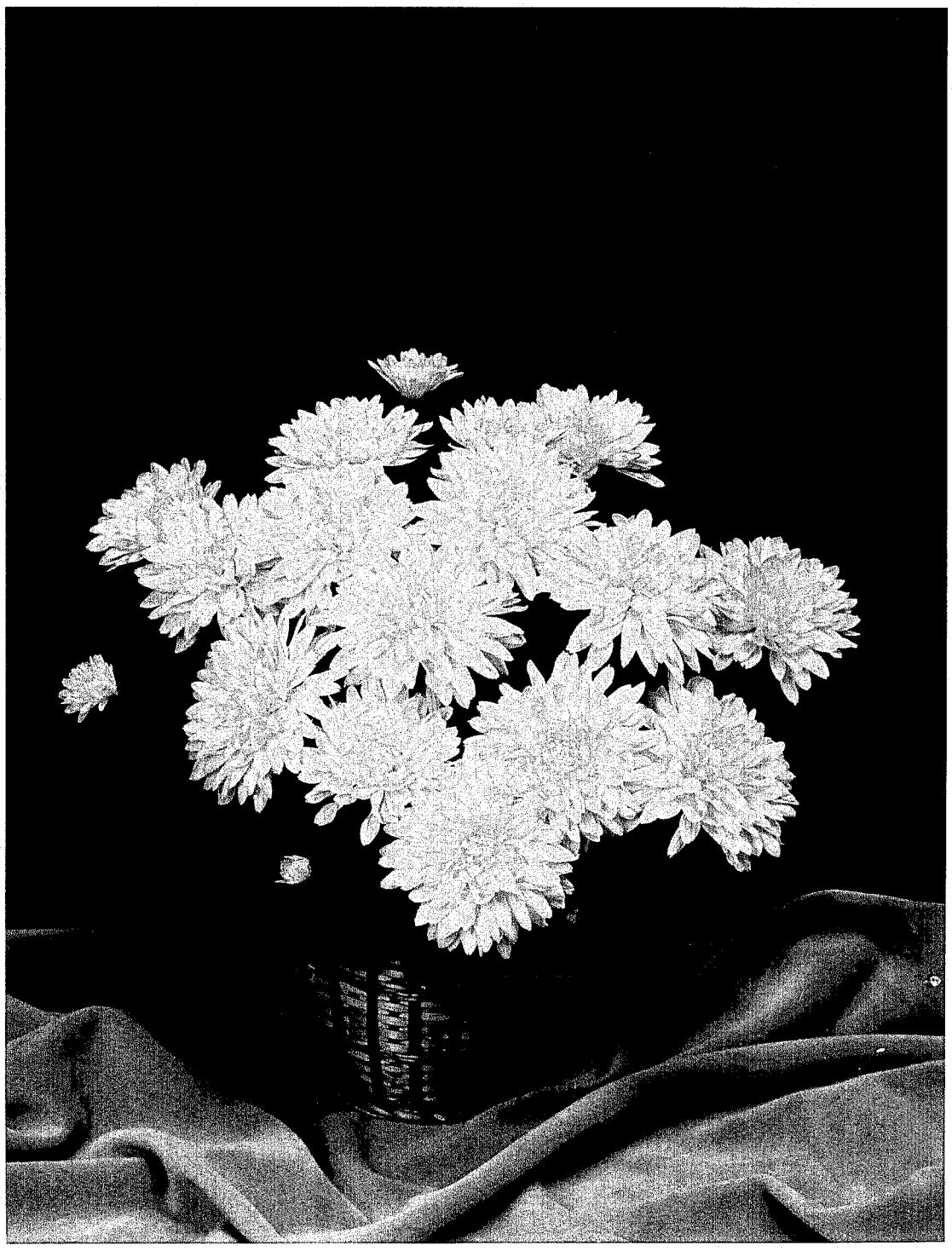

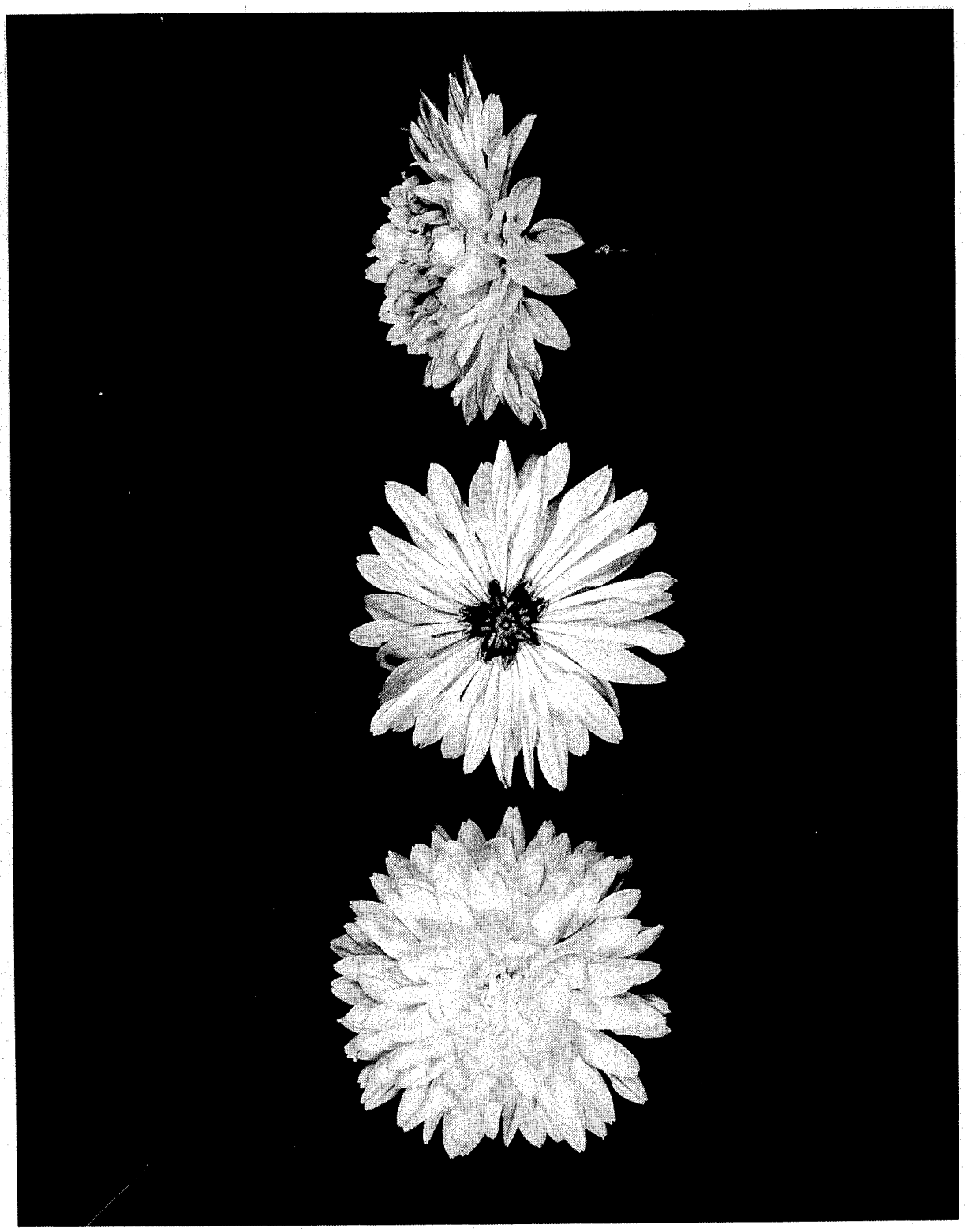

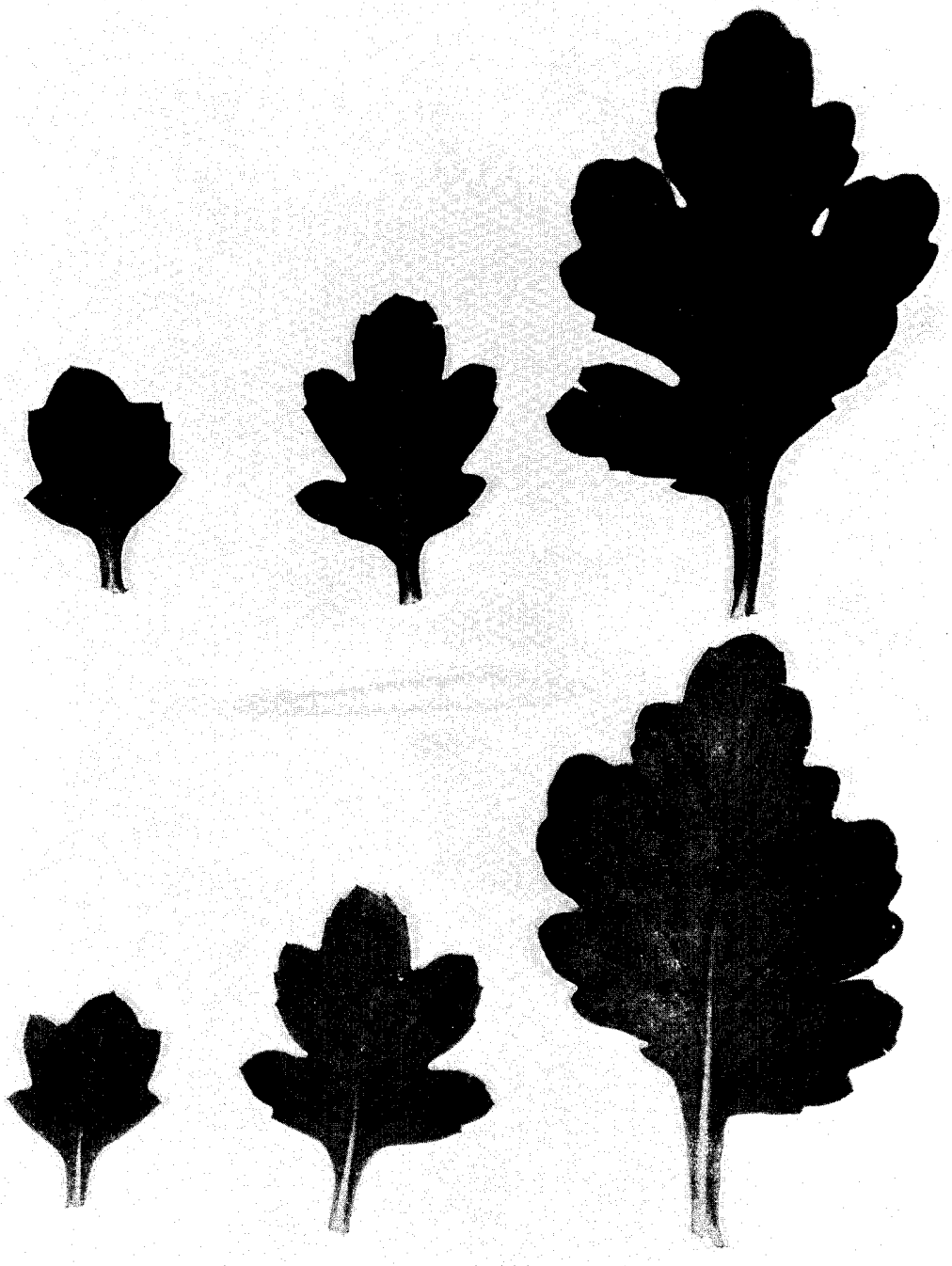

UNITED STATES PATENT AND TRADEMARK OFFICE

CERTIFICATE OF CORRECTION

PATENT NO. : Plant 6,949

DATED : July 25, 1989

INVENTOR(S) : Cornelis P. VandenBerg

It is certified that error appears in the above—identified patent and that said Letters Patent is hereby corrected as shown below:

Column 3, line 6, "Other" should be changed to --Outer--.

Column 3, line 8, "first" should be changed to --flat--.

Signed and Sealed this

Twelfth Day of March, 1991

*Attest:*

HARRY F. MANBECK, JR.

*Attesting Officer*

*Commissioner of Patents and Trademarks*